US006430987B1

(12) United States Patent
Stark

(10) Patent No.: US 6,430,987 B1
(45) Date of Patent: Aug. 13, 2002

(54) APPARATUS AND METHOD FOR MEASURING THE CONCENTRATION OF A PARAMAGNETIC GAS

(75) Inventor: Hartmut Stark, Stockelsdorf (DE)

(73) Assignee: Drager Medizintechnik GmbH (DE)

( * ) Notice: Subject to any disclaimer, the term of this patent is extended or adjusted under 35 U.S.C. 154(b) by 0 days.

(21) Appl. No.: 09/698,233

(22) Filed: Oct. 30, 2000

(30) Foreign Application Priority Data

| Oct. 30, 1999 | (DE) | 199 52 373 |
| Aug. 1, 2000 | (DE) | 100 37 380 |

(51) Int. Cl.$^7$ .............................................. G01N 27/74
(52) U.S. Cl. ...................... 73/25.02; 73/25.03; 324/204
(58) Field of Search ............................ 73/25.02, 25.03; 324/204

(56) References Cited

U.S. PATENT DOCUMENTS

| 2,472,645 A | * | 6/1949 | Clark | 73/25.02 |
| 3,064,465 A | * | 11/1962 | Richardson | 73/25.02 |
| 3,276,244 A | * | 10/1966 | Wilson et al. | 73/25.02 |
| 3,435,662 A | * | 4/1969 | Meyer | 73/25.02 |
| 5,012,669 A | | 5/1991 | Meyer | |
| 5,269,170 A | * | 12/1993 | Meyer | 324/204 |
| 5,493,215 A | * | 2/1996 | Otten | 324/204 |
| 6,071,008 A | | 6/2000 | Hatta | |

FOREIGN PATENT DOCUMENTS

| DE | 198 03 191 | | 7/1998 | |
| DE | 197 03 892 | | 8/1998 | |
| DE | 198 46 917 | | 6/1999 | |
| GB | 0588496 | * | 5/1947 | 73/25.02 |
| GB | 2 332 072 | | 11/1999 | |
| JP | 0139799 | * | 10/1979 | 73/25.02 |

OTHER PUBLICATIONS

Dyer, Clarence A. "A Paramagnetic Oxygen Analyzer" Review of Scientific Instruments, vol. 18, No. 10, pp. 696–702, Oct. 1947.*
Abstract of Borman, V.D.; 81:178984 "Thermal conductivity of oxygen in parallel stationary and varying magnetic fields at low pressure"; 1974.
Fleming et al; "Resonant Transport Properties of Polyatomic Gases in Oscillating Manetic Fields"; The Journal of Chemical Physics, vol. 56, No. 1; Jan. 1972; pp. 52–69.
H. Torwegge, "Die Einwirkung magnetischer Felder auf das Wärmeleitvermögen von NO und $NO_2$" ["The Influence of Magnetic Fields on the Thermal Conduction Capacity of NO and $NO_2$"], Annalen der Physik ["Annals of Physics"], 5th series, vol. 33, 1938, pp. 459–470.

* cited by examiner

*Primary Examiner*—Hezron Williams
*Assistant Examiner*—Michael Cygan
(74) *Attorney, Agent, or Firm*—Nixon & Vanderhye PC

(57) ABSTRACT

The object is to improve an apparatus for measuring the concentration of a paramagnetic gas in a gas sample, in such a way a measurement signal with a low noise ratio is obtained. The apparatus proposed according to the invention is characterized by a modulatable magnetic field source 4, 5, 6, 7 with an air gap 3 as a measuring chamber for receiving the gas sample; a modulation source 26 for outputting a modulation signal to the magnetic field source 4, 5, 6, 7; a measuring element 8, disposed inside the air gap 3 and heated to an operating temperature, for outputting a heat flow measurement signal; a filter device 28, 29, for filtering periodic fluctuations out, caused by the modulation of the magnetic field source, from the heat flow measurement signal caused by the modulation of the magnetic field source, the amplitude of the periodic fluctuations, being a measure for the proportion of the gas in the gas sample.

25 Claims, 12 Drawing Sheets

APPARATUS AND METHOD FOR MEASURING THE CONCENTRATION OF A PARAMAGNETIC GAS

CROSS-REFERENCES TO RELATED APPLICATIONS

This application is based on and claims priority of German patent application No. 19952373.8 filed on Oct. 30, 1999 and German patent application No. 10037380.1 filed on Aug. 1, 2000, the disclosures of each of which are incorporated herein by reference in their entirety.

BACKGROUND OF THE INVENTION

1. Field of the Invention

The invention relates to an apparatus and a method for measuring the concentration of a paramagnetic gas in a gas sample, especially oxygen in respiratory gas.

2. Description of the Related Art

From the publication by H. Torwegge entitled "Die Einwirkung magnetischer Felder auf das Wärmeleitvermögen von NO und $NO_2$" ["The Influence of Magnetic Fields on the Thermal Conduction Capacity of NO and $NO_2$"], Annalen der Physik ["Annals of Physics"], 5th series, Vol. 33, 1938, pages 459–470, it is known that paramagnetic gases vary their thermal conductivity under the influence of magnetic fields. The reason for this behavior is evidently the fact that paramagnetic gases possess a permanent magnetic moment, which however normally, because of the thermal molecular motion of the gas molecules, is not apparent from outside. These conditions change if a sufficiently strong, external magnetic field assures that the magnetic moments of the individual molecules are oriented. On the one hand, this causes a change in susceptibility, which leads to an increase in the magnetic flux; on the other hand, a certain molecular order ensues in the gas, thereby limiting the capability of transmitting heat energy to adjacent molecules by impacts. This changes the thermal conductivity slightly.

In the known apparatus, the gas sample to be examined is located in a cylindrical vessel, in whose longitudinal axis a thin measuring wire, heated to an operating temperature, is disposed. If the thermal conductivity of the gas varies because of an external magnetic field, this causes a change in resistance of the measuring wire, which can be determined with a measurement bridge. A disadvantage of the known apparatus is that because of the requisite precision in detecting temperature changes of the measuring wire, very stringent demands must be made of the resistance measurement. This makes it impossible to distinguish the actual measurement signal unequivocally from the noise variables and drift factors that are always present.

SUMMARY OF THE INVENTION

It is the object of the invention to improve an apparatus of the type defined above in such a way that the noise variables that impair the measurement signal are largely eliminated, and to disclose a method for performing the measurement.

The object with regard to the apparatus is attained with the characteristics of claim 1. This object is also attained with the characteristics of claims 16, 19, 21, and 22.

The object with regard to the method is attained with the characteristics of claim 14.

In the measuring apparatus of the invention, the measuring element, heated to the operating temperature, is disposed in a modulated magnetic field, and the periodic fluctuations of the heat flow measurement signal that occurs at the measuring element and that are based on the modulation of the magnetic field source are evaluated. The periodic fluctuations of the heat flow measurement signal are especially simple to distinguish from the background signal by means of a filter device. By selective evaluation of the periodic fluctuations, noise factors are largely eliminated, since the effects of drift and temperature are contained predominantly in the direct component of the heat flow measurement signal.

The heat flow to be evaluated, that is, the quantity of heat dissipated from the measuring element to the gas sample, is composed of the thermal conduction and the thermal capacity of the gas sample together and is dependent on the proportion of the paramagnetic gas.

The magnetic field can be modulated mechanically, for instance with rotating permanent magnets, or electrically. For the electrical modulation, alternating voltages that are low in harmonics, such as sine wave voltages, are especially suitable.

It is especially advantageous, instead of a single magnetic field source, to use two modulatable magnetic field sources and to connect them in alternation to the modulation source, so that at all times, one magnetic field source is free of current and the other is acted upon by the modulation current. The measuring element is disposed inside the air gaps of the magnetic field sources and for the case of a thermocouple arrangement has opposed first and second connection points. Depending on the current imposed on the magnetic field sources, the connection points, which are heated to the same working temperature, which is elevated compared to the temperature of the gas sample, act as a measuring and compensation element. In the presence of a paramagnetic gas in the measuring chamber formed by the air gaps, the thermal conduction in the air gap of the magnetic field source on which current is imposed decreases, resulting in a corresponding temperature increase and leading to a differential temperature between the connection points. This differential temperature can be measured as the thermocouple voltage. It is especially advantageous that fluctuations in thermal conduction of the gas sample stream have the same effect on both connection points and are thus compensated for.

Advantageous features of the invention are defined by the dependent claims.

For measuring the heat flow from the measuring element to the gas sample, an arrangement of one or more thermocouples, which are placed in the air gap inside the magnetic field, has proved especially advantageous. In a thermocouple arrangement with three connection points, one of the connection points is for instance located in the center of the wire, while the other two connection points are disposed at the support wires leading to the thermocouple arrangement. If the thermocouple arrangement is now heated by an alternating current source to an operating temperature elevated compared to the temperature of the gas sample, then this heats the support wires only insignificantly, because they are dimensioned substantially thicker than the thermocouple wire. Thus the connection points placed at the support wires are approximately at the ambient temperature level. The thermocouple voltage, as the intrinsic electromotive force (EMF) of the thermocouple arrangement, is thus proportional to the operating temperature of the thermocouple wire. Since the thermocouple voltage remains substantially uninfluenced by the intensity of the magnetic field, the temperature measurement is not interfered by the magnetic field modulation.

It is especially advantageous to utilize the thermocouple voltage to regulate the alternating current source. If the temperature difference between the thermocouple arrangement and the gas sample to be examined is regulated to a constant value, then the electrical power required for this corresponds to the quantity of heat dissipated by thermal conduction into the gas sample and via the support wires.

As an alternative to regulating to a constant temperature difference between the thermocouple arrangement and the gas sample, the electrical power, converted in the thermocouple arrangement, or the heating alternating current, heating alternating voltage, or Ohmic resistance of the thermocouple arrangement can be kept constant, and the thermocouple voltage that ensues can be further processed as the heat flow measurement signal.

Besides the electrical modulation of the magnetic field source, the possibility exists of varying the magnetic field with a rotating chopper disk of soft magnetic or permanent magnetic material disposed inside the air gap.

An advantageous method for measuring the proportion of a paramagnetic gas in a gas sample comprises disposing a measuring element, heated to an operating temperature, in an air gap, receiving the gas sample, of a modulated magnetic field source; determining a heat flow measurement signal from the heat flow from the measuring element to the gas sample; with a filter device, filtering out periodic fluctuations from the heat flow measurement signal that are caused by the modulation of the magnetic field source; and from the periodic fluctuations, determining a concentration measurement value that indicates the proportion of the gas.

Especially advantageously, with the method disclosed according to the invention, oxygen concentrations in medical therapeutic appliances can be determined, since in contrast to the electrochemical sensors usually used in such equipment, the measuring element is not subject to any wear.

One exemplary embodiment of the invention is shown in the drawing and described in further detail hereinafter.

DESCRIPTION OF THE EXEMPLARY EMBODIMENTS

Figure 1:
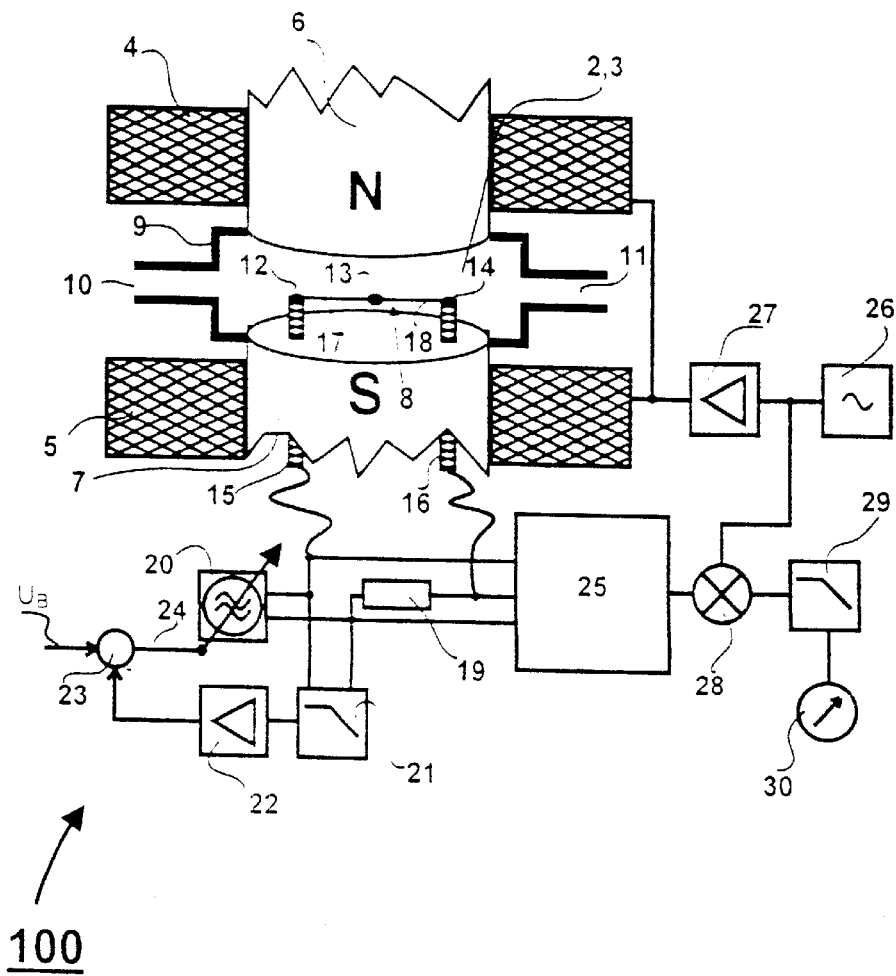
FIG. 1 schematically shows the layout of a paramagnetic gas sensor in a first measuring apparatus.

FIG. 1 schematically shows the layout of a first measuring apparatus 100, in which, in an air gap 3 embodied as a measuring chamber 2 of a magnetic field source comprising field coils 4, 5 and pole pieces 6, 7, a thermocouple 8 is disposed. The measuring chamber 2 is defined by the pole pieces 6, 7 and by a wall 9, located between the pole. pieces 6, 7, that has a measuring chamber inlet 10 and a measuring chamber outlet 11. The thermocouple 8 with the connection points 12, 13, 14 is fastened to two support wires 15, 16, which are passed through the lower pole piece 7; the connection points 12, 14 are located at the support wires 15, 16, while the connection point 13 is disposed approximately in the middle of the thermocouple 8. The thermocouple 8 comprises two wire segments 17, 18, which abut one another at the connection point 13. Via a series resistor 19, the thermocouple 8 is connected to an alternating current source 20, by which it is heated to an operating temperature that is elevated compared with the temperature of the gas sample located in the measuring chamber 2. With this wiring of the thermocouple 8, an alternating voltage signal is applied to the support wires 15, 16, and superimposed on this signal is the intrinsic EMF of the thermocouple 8, hereinafter called the thermocouple voltage. The thermocouple voltage is filtered out of the alternating voltage signal by means of a low-pass filter 21, raised to a higher signal level with an amplifier 22, and compared as a controlling variable with a reference voltage $U_B$ at a comparison point 23; the reference voltage, as a set-point temperature value, is proportional to the operating temperature of the thermocouple 8. The differential signal, comprising the amplified thermocouple voltage and the reference voltage $U_B$ that occurs at the output 24 of the comparison point 23 is delivered as an adjusting variable to the alternating current source 20. The thermocouple 8 with the series resistor 19, the low-pass filter 21, the amplifier 22, the comparison point 23, and the alternating current source 20 together form a first closed control circuit, with which the temperature of the thermocouple 8 is regulated to a constant value.

The measurement of the operating temperature with the thermocouple 8 is due to the fact that the connection point 13 of the thermocouple 8 detects the temperature in the middle of the wire, while the connection points 12, 14 are located on the substantially thicker support wires 15, 16, which are heated hardly at all by the heating current and are moreover located in direct thermal contact with the pole piece 7 and are thus at the ambient temperature level.

The voltage drop that occurs at the series resistor 19, which is proportional to the alternating current flowing through the thermocouple 8, and the alternating voltage signal applied to the support wires 15, 16 are delivered to a power measuring device 25, with which the electrical power delivered to the thermocouple 8 is determined.

The thermal conductivity measurement with the thermocouple 8 is performed under the influence of a periodically varying magnetic field. To that end, a modulation source 26 is connected to the field coils 4, 5 via a power amplifier 27. The modulation source 26 outputs a sinusoidal voltage as its modulation signal to the field coils 4, 5. As a result of the modulated magnetic field, periodic fluctuations in the quantity of heat dissipated from the thermocouple 8 to the gas sample occur; this quantity of heat is dependent on the concentration of the paramagnetic gas to be detected. These periodic fluctuations are superimposed on the background signal of the heat flow. Distinguishing the periodically varying heat flow measurement signal from the background heat flow signal is effected in a phase-sensitive rectifier. downstream of the power measuring device 25, in the form of a lock-in amplifier 28, which as a further input signal receives the modulation signal of the modulation source 26.

As a result of the multiplicative linking of the modulation signal with the measurement signal, the heat flow measurement signal, periodically varying with the modulation of the field coils 4, 5, drops at the output of the lock-in amplifier 28 as a direct voltage, on which an alternating voltage component is superimposed. This alternating voltage component can be eliminated by a smoothing device 29, so that the direct voltage component and thus a measurement value dependent on the concentration of the paramagnetic gas in the gas sample are shown on a gauge or display.

Figure 2:
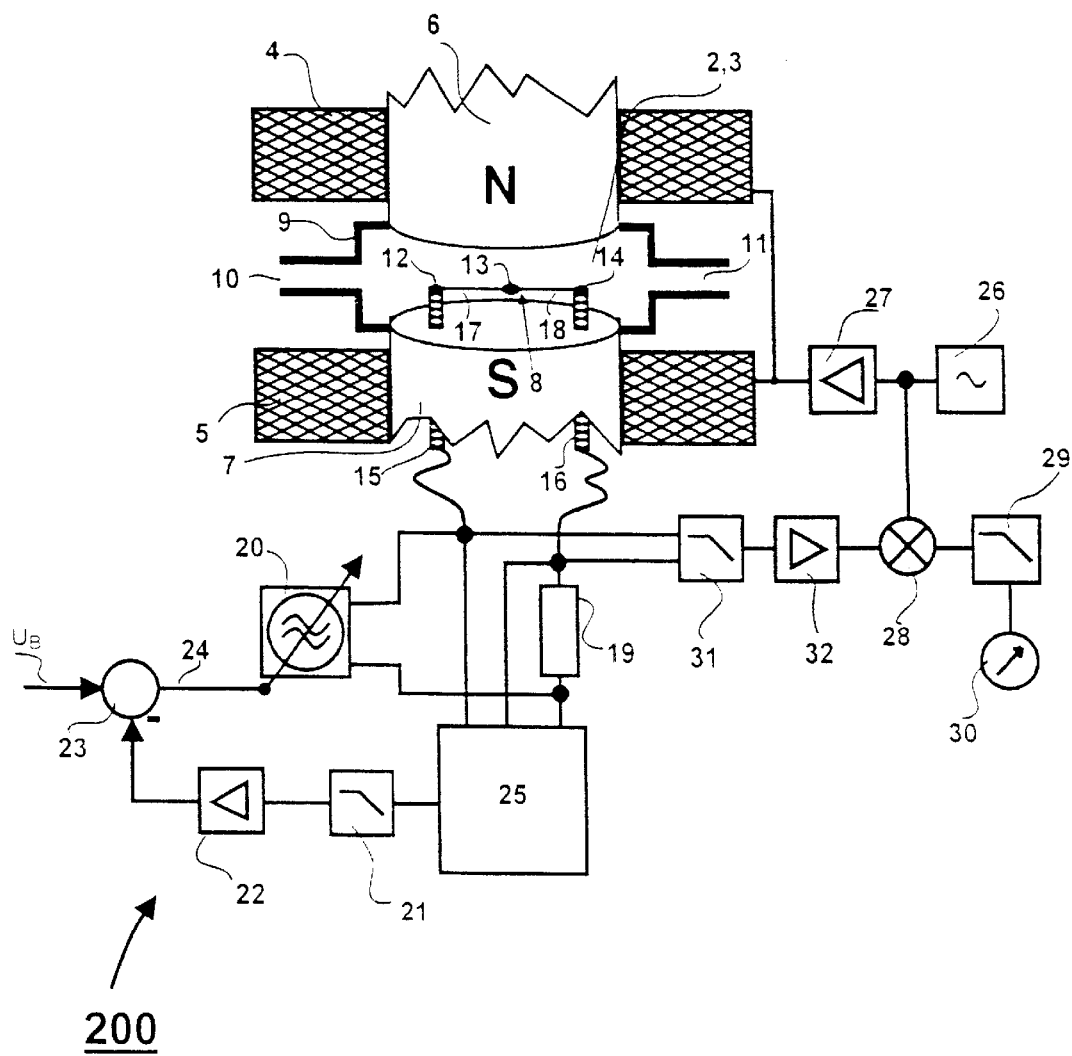
FIG. 2 schematically shows a second measuring apparatus.

In a second measuring apparatus 200, shown in FIG. 2, compared to the first measuring apparatus 100, the power converted in the thermocouple 8 is regulated to a constant value with a second closed control circuit 8, 19, 20, 21, 22, 23, 25. To that end, the output signal of the power measuring device 25 is delivered as a controlling variable to the comparison point 23. The voltage occurring at the thermocouple 8 is extracted by means of a low-pass filter 31 from the alternating voltage component caused by the alternating current source 20, before the component reaches, via an amplifier 32, the lock-in amplifier 28.

Figure 3:
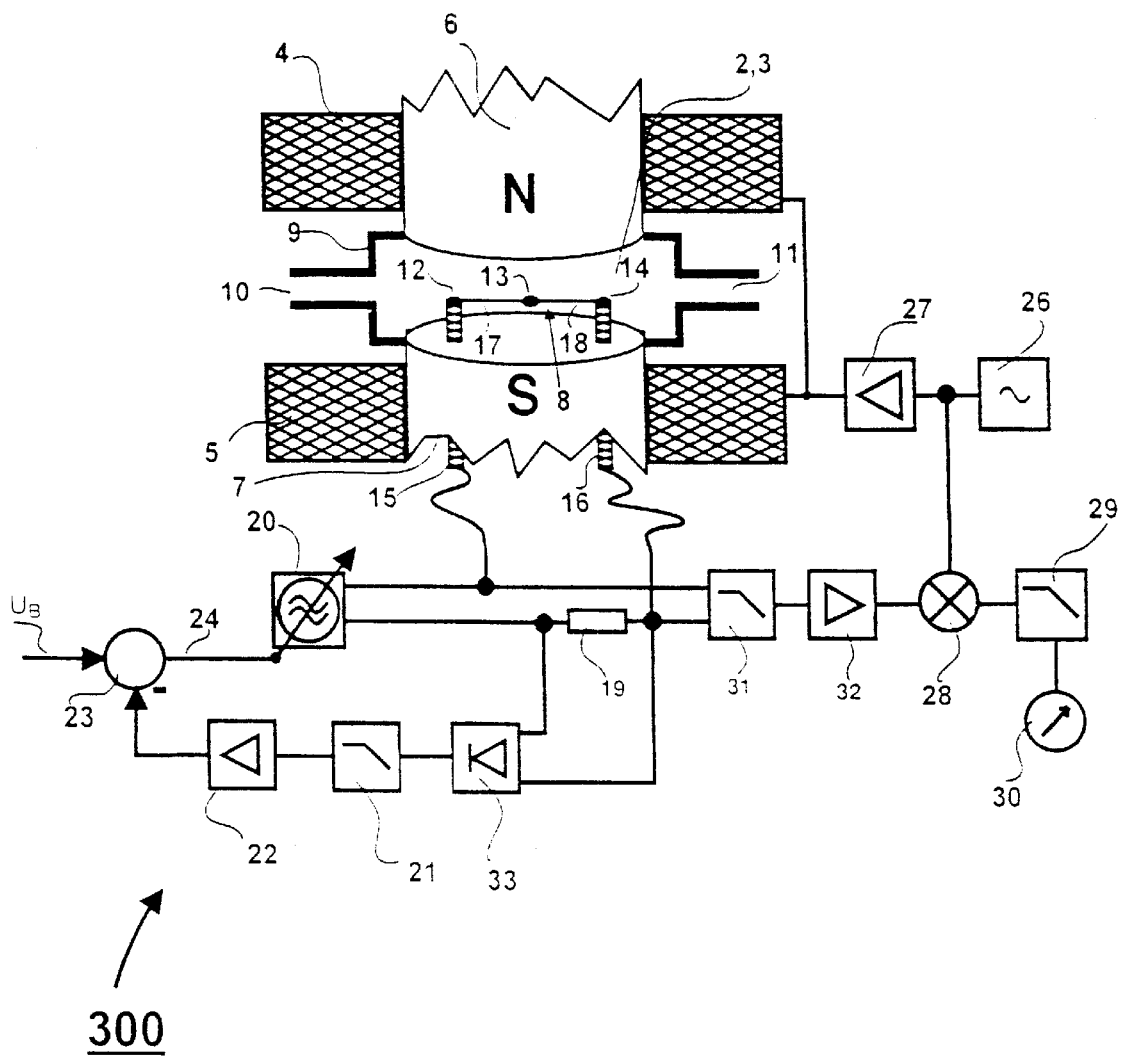
FIG. 3 schematically shows a third measuring apparatus.

The third measuring apparatus 300, shown in FIG. 3, differs from the measuring apparatuses 100, 200 in regulating the heating current, flowing through the thermocouple 8, to a constant value by means of a third closed control circuit 8, 19, 20, 21, 22, 23, 33. As a variable proportional to the heating current, the voltage dropping at the series resistor 19 is rectified by means of the diode 33, filtered with the low-pass filter 21, and supplied as a controlling variable to the comparison point 23.

Figure 4:
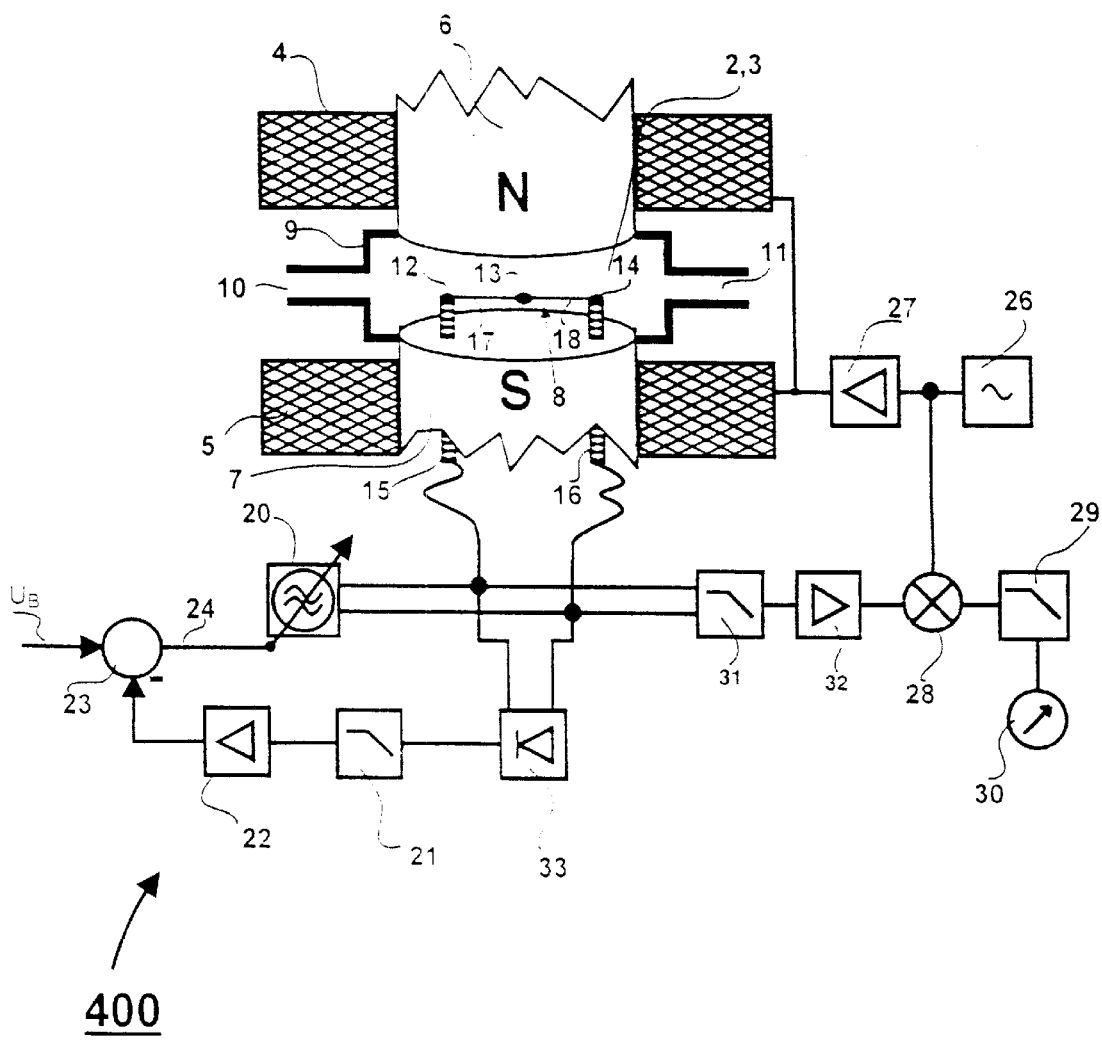
FIG. 4 schematically shows a fourth measuring apparatus.

In a fourth measuring apparatus 400. shown in FIG. 4, with a fourth closed control circuit 8, 20, 21, 22, 23, 33, a regulation of the heating voltage applied to the thermocouple 8 to a constant value is performed. Identical components are identified by the same reference numerals as in FIGS. 2 and 3.

Figure 5:
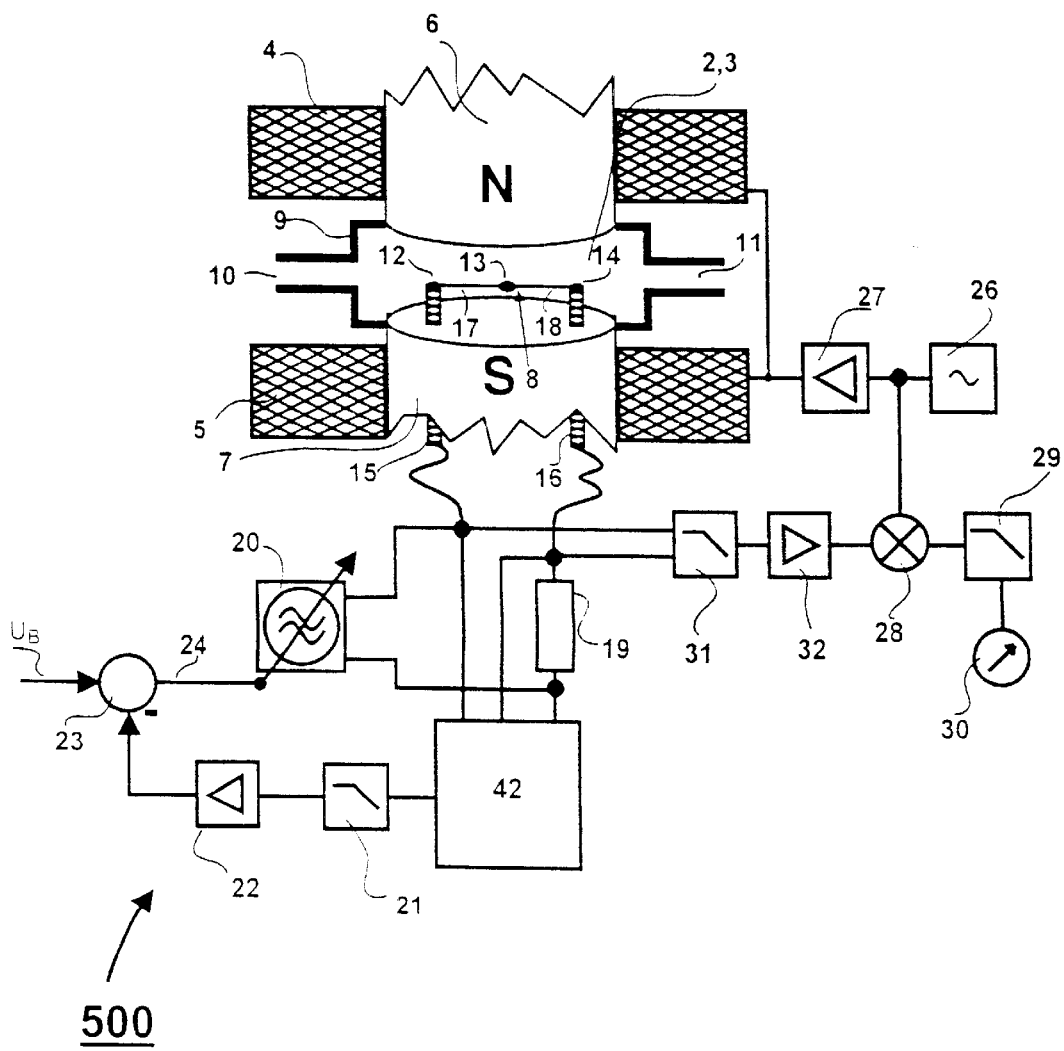
FIG. 5 schematically shows a fifth measuring apparatus.

In FIG. 5, a fifth measuring apparatus 500, with a fifth closed control circuit 8, 19, 20, 21, 23, 42, is shown in which the temperature of the thermocouple 8 is kept at a constant value by regulation of the thermocouple resistance. To that end, the resistance of the thermocouple 8 is ascertained with a resistance measuring instrument 42 and is supplied as a controlling variable to the comparison point 23.

Figure 6:
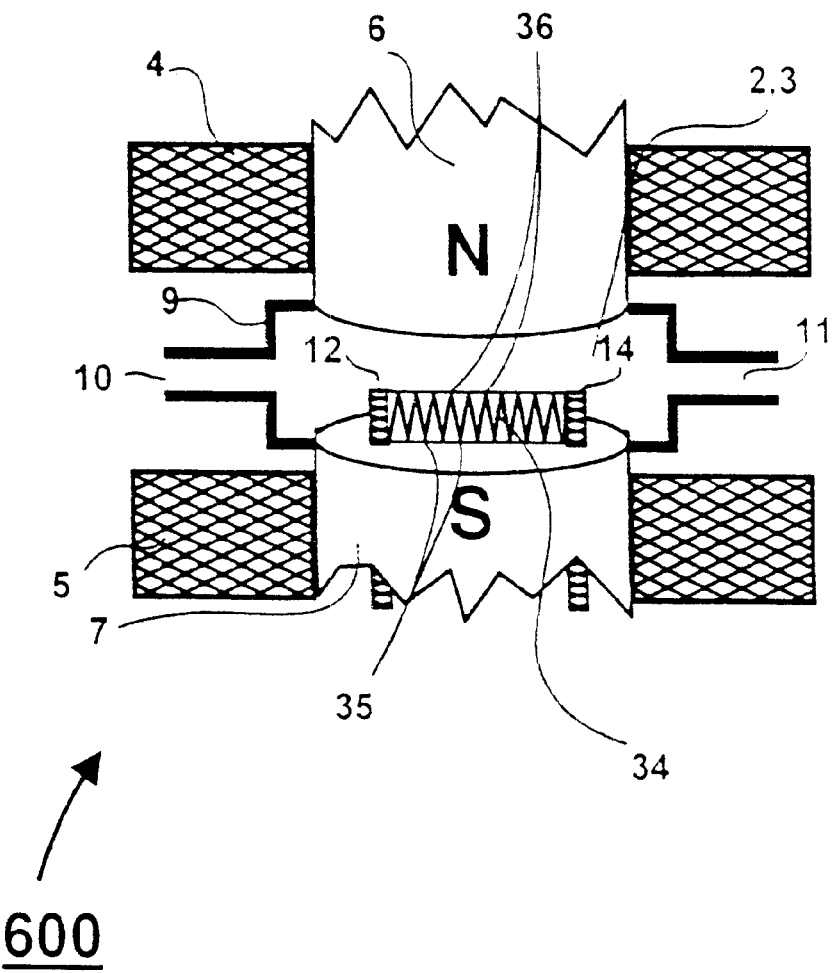
FIG. 6 schematically shows a sixth measuring apparatus with a thermopile as the measuring sensor.

FIG. 6 in fragmentary form shows a sixth measuring apparatus 600, in which identical thermocouples 8 are combined into a thermopile 34, with connection points 35 on the underside and connection points 36 on the top side. For the sake of greater clarity, in FIG. 6 only some of the connection points 35, 36 are provided with reference numerals. The connection points 35 on the underside are in thermal contact with the pole piece 7 and are thus at the ambient temperature level, while the connection. points 36 are heated to the operating temperature.

Compared to an arrangement with individual thermocouples, the thermopile 34 results in a substantially higher temperature signal and thus a markedly improved signal to noise ratio for measuring the closed control circuit.

Figure 7:
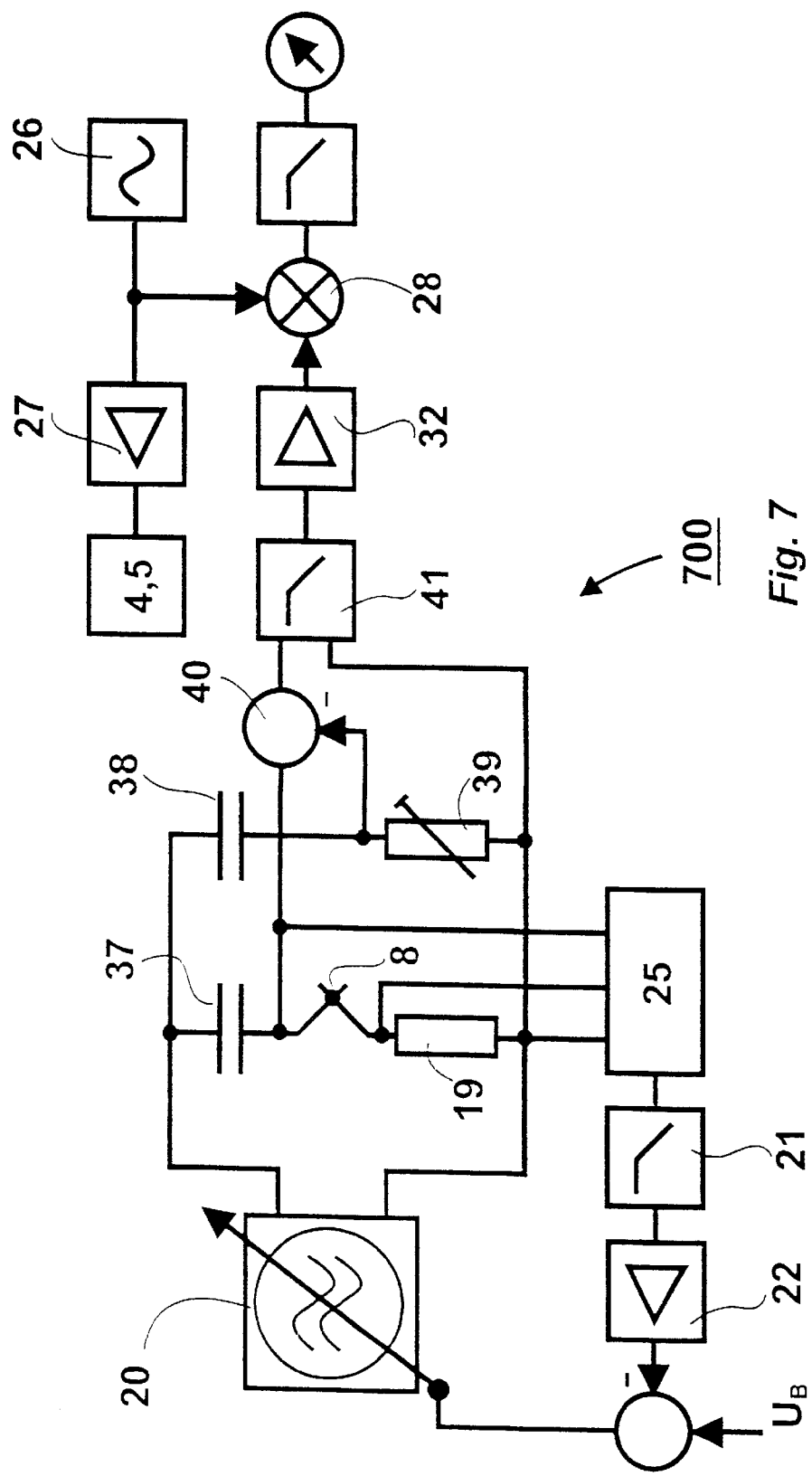
FIG. 7 shows a seventh measuring apparatus as an alternative to the second measuring apparatus.

An improved capability, compared with the second measuring apparatus 200 in FIG. 2, for eliminating the heating alternating voltage is to obtain the alternating voltage component, caused by the alternating current source 20, in the thermocouple voltage not with the low-pass filter 31 but rather by phase-correct subtraction of the heating voltage components. A seventh measuring apparatus 700 of this kind is shown in FIG. 7.

Via a capacitor 37 and the series resistor 19, the thermocouple 8 is supplied with the heating current. By parallel connection of a further capacitor 38 with a bridge resistor 39, a voltage can now be obtained that, given suitable calibration of the bridge resistor 39, agrees in amount and phase with the voltage dropping across the components 8, 19.

By suitable subtraction of the voltages at a subtractor 40, the thermocouple voltage of interest can be obtained; it now contains only a slight alternating voltage component, which can eliminated with a simplified filter circuit 41.

Identical components are provided with the same reference numerals as in FIG. 2.

The gas sensor 1 proposed according to the invention is especially suitable for detecting oxygen, and compared to other measuring methods that utilize the paramagnetic effect, it has the advantage in electrical modulation of the magnetic field of having no moving parts, such as cuvettes, and as a result has a virtually unlimited service life.

Figure 8:
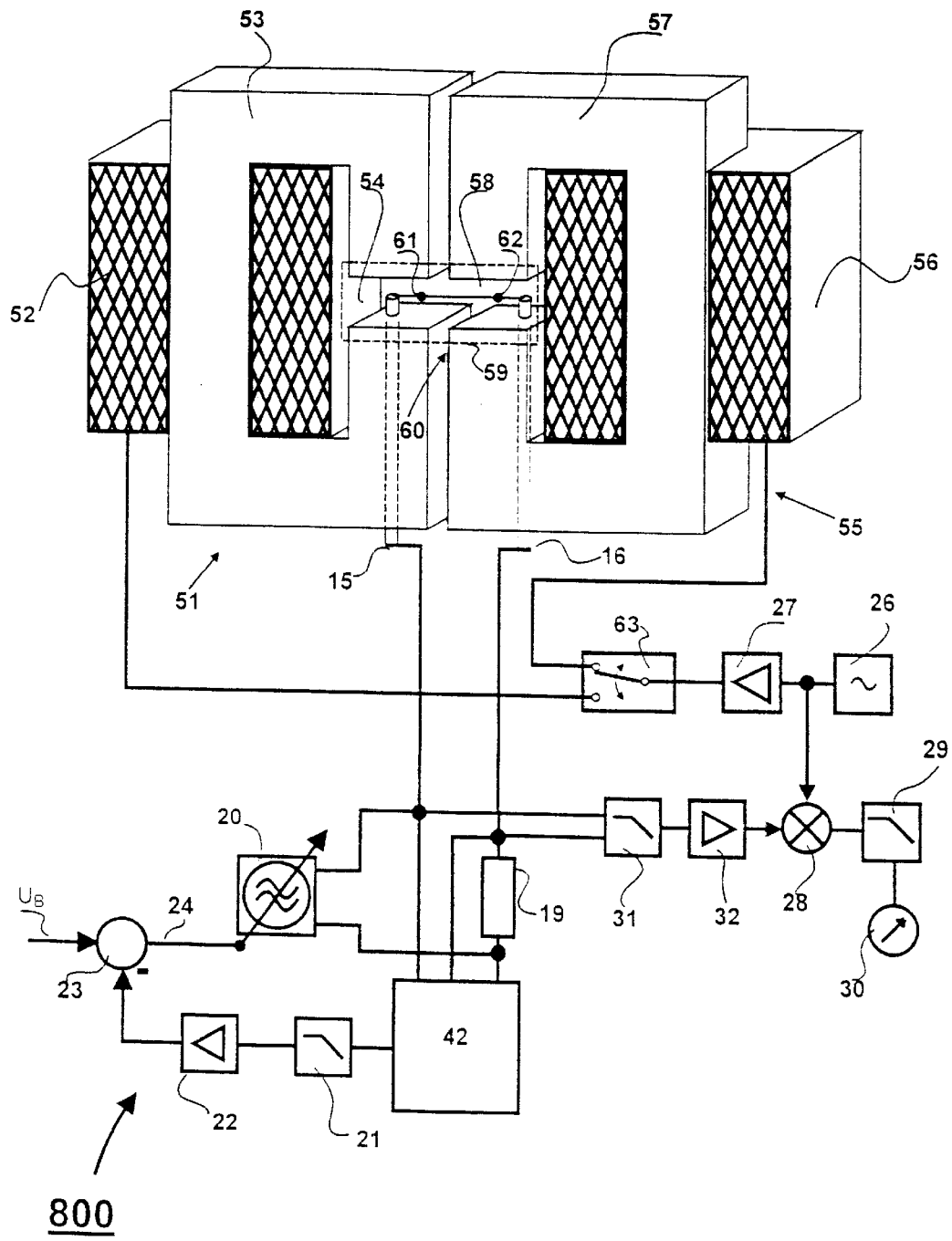
FIG. 8, an eighth measuring apparatus with two magnetic field sources.

FIG. 8 schematically shows an eighth measuring apparatus 800, in which instead of a single magnetic field source, a first magnetic field source 51, with a first field coil 52, first pole pieces 53 and a first air gap 54, and a second magnetic field source 55, with a second field coil 56, second pole pieces 57 and a second air gap 58, are provided. The first and second air gaps 54, 58 are located in a measuring chamber 59, which is filled with the gas sample to be examined. The measuring chamber 59 is represented only by a dashed line in FIG. 8, for the sake of simplicity. A thermocouple arrangement 60 with a first connection point 61 in the first air gap 54 and a second connection point 62 in the second air gap 58 is located on two support wires 15, 16 in the measuring chamber 59. The field coils 52. 56 are connected in alternation to the modulation source 26 via a reversing switch 63. The reversing switch 63 is triggered such that the positive half-waves of the modulation signal are each carried to the first magnetic field source 51, and the negative half-waves are carried to the second magnetic field source 55. With a closed control circuit formed by the components 19, 20, 21, 23, 42, 60, the temperature of the thermocouple arrangement 60 is kept at a constant value, in that the resistance of the thermocouple arrangement 60 is ascertained with the resistance measuring instrument 42 and carried as a controlling variable to the comparison point 23. Identical components are identified by the same reference numerals as in FIG. 5. The operating temperature of the thermocouple arrangement 60 is preferably about 100 degrees celsius, and the temperature of the gas sample to be examined is on the order of magnitude of about 20 degrees celsius. In the eighth measuring apparatus 800, the connection points 61, 62 are at the same temperature level, so that fluctuations in the thermal conduction in the gas sample stream in a first approximation have the same effect on the connection points 61, 62 and are thus compensated for. The connection points 61, 62 of the thermocouple arrangement 60 each form one measuring element and one compensation element, depending on the current flow in the field coils 52, 56. By the alternating application of current to the field coils 52, 56 by means of the reversing switch 63, the measuring element and compensation element are cyclically transposed, and the compensation element in each case is located in whichever air gap is free of a magnetic field at the time. In the switch position of the reversing switch 63 shown in FIG. 8, the first field coil 52 is current-free, and the second field coil 56 is connected to the modulation source 26. Thus the first connection point 61 is the compensation element, and the second connection point 62 is the measuring element. It a paramagnetic gas is present in the measuring chamber 59, the thermal conduction decreases in the region of high magnetic field intensities, in the present case in the region of the second air gap 58, and this causes a corresponding temperature increase.

This temperature increase at the second connection point 62 compared to the first connection point 61 can then be measured as the thermocouple voltage. After signal filtration by means of the lock-in amplifier 28, the proportion of the gas to be detected in the gas sample can be read out at the gauge or display device 30. In the next operating cycle, the first field coil 52 is connected to the modulation source 26, and the second field coil 56 is current-free. The first connection point 61 is then the measuring element, and the second connection point 62 is the compensation element.

The arrangement shown in FIG. 8, by means of two magnetic field sources 51, 55 connected in alternation to the modulation source 26, and by means of the arrangement of connection points 61, 62 in the first air gap 54 of the first magnetic field source 51 and in the second air gap 58 of the second magnetic field source 55, respectively, has the advantage that temperature fluctuations in the gas sample stream have the same effect in a first approximation on both connection points 61, 62 and are thus compensated for. In addition, the undesired variations in thermal conduction, caused by the magnetic field, in the usually ferromagnetic alloys of the thermocouple materials have hardly any further effect, since they can affect only the heat transport from the warmer connection point to the colder connection point. This temperature difference, however, is markedly less than the temperature difference between the thermocouple arrangement 60 and the gas sample.

A further improvement is attained by incorporating an ideally freely floating thermopile 64, with opposed first connection points 65 and second connection points 66 in the measuring chamber 59. By fastening the thermopile 64 to support wires, not shown, the heating power can be reduced still further, since no heat is dissipated via the support wires. An arrangement with a thermopile 64 is shown as the ninth measuring apparatus 900 in FIG. 9. Identical components are identified by the same reference numerals as in FIG. 8.

Figure 9:
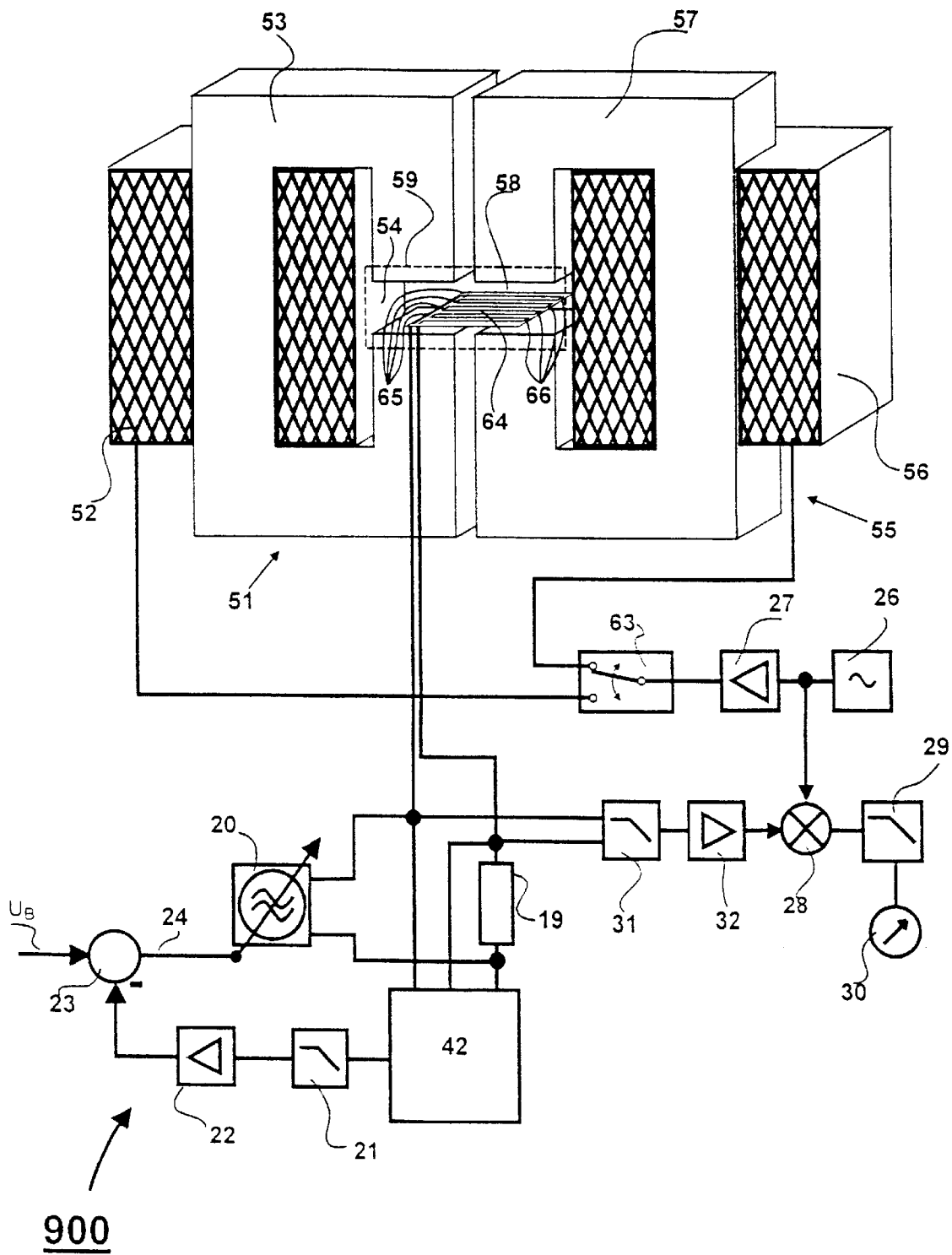
FIG. 9, a ninth measuring apparatus as an alternative to the measuring apparatus of FIG 8.
Figure 10:
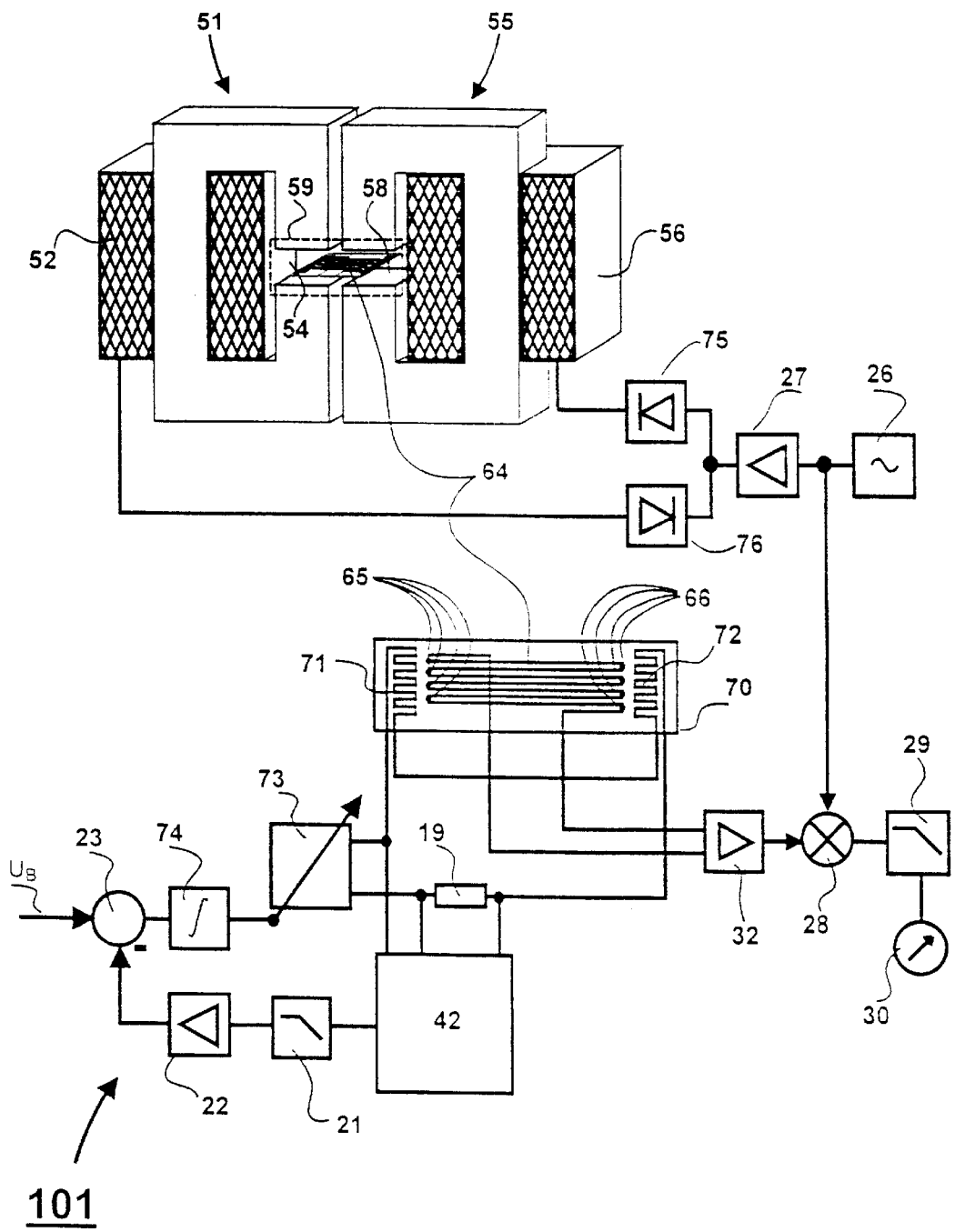
FIG. 10, a tenth measuring apparatus with a separate heating element for the thermocouple arrangement.

A tenth measuring apparatus 101 shown in FIG. 10 differs from the ninth measuring apparatus 900 in FIG. 9 in that in addition to the thermopile 64, a first heating resistor 71 in the region of the first connection points 65 and a second heating resistor 72 in the region of the second connection points 66 are mounted on a measuring element carrier 70. The first heating resistor 71 is located together with the first connection points 65 in the first air gap 54, while the second heating resistor 72 is disposed along with the second connection points 66 in the second air gap 58. For the sake of greater clarity, the measuring element carrier 70 is shown in FIG. 10 enlarged, outside the measuring chamber 59.

Identical components are identified by the same reference numerals as in FIG. 9.

The heating resistors 71, 72 are connected via the series resistor 19 to a heating current source 73, which can be embodied as either a direct or alternating current source. The heating current source 73 receives the adjusting variable from an integrator 74. By means of a closed control circuit, formed by the components 19, 21, 22, 23, 42, 71, 72, 73, the heating resistors 71, 72 are regulated to a constant resistance, which is proportional to the reference voltage $U_B$. With the heating resistors 71, 72, the thermopile 64 is heated to an operating temperature that is elevated compared to the temperature of the gas sample. The field coils 52, 56 are supplied with the modulation signal via diodes 75, 76. The diodes 75, 76, which serve as reversing switch means for the modulation voltage, are connected such that the diode 75 in each case admits the positive half-wave of the modulation signal furnished by the modulation source 26, and the diode 76 admits the negative half-wave. By means of the diodes 75, 76, the field coils 52, 56 are turned on and off in alternation.

In the presence of a paramagnetic gas, the thermal conductivity varies in whichever air gap has its field coil acted upon by the modulation signal. This leads to a temperature difference between the connection points 65, 66, which can be measured as the thermocouple voltage with the thermopile 64. After a phase-sensitive rectification in the lock-in amplifier 28 and elimination of the alternating voltage component as a result of the magnetic field modulation by the smoothing device 29, the direct voltage component, which is proportional to the concentration of the paramagnetic gas in the gas sample, can be read from the gauge or display device 30.

Figure 11:
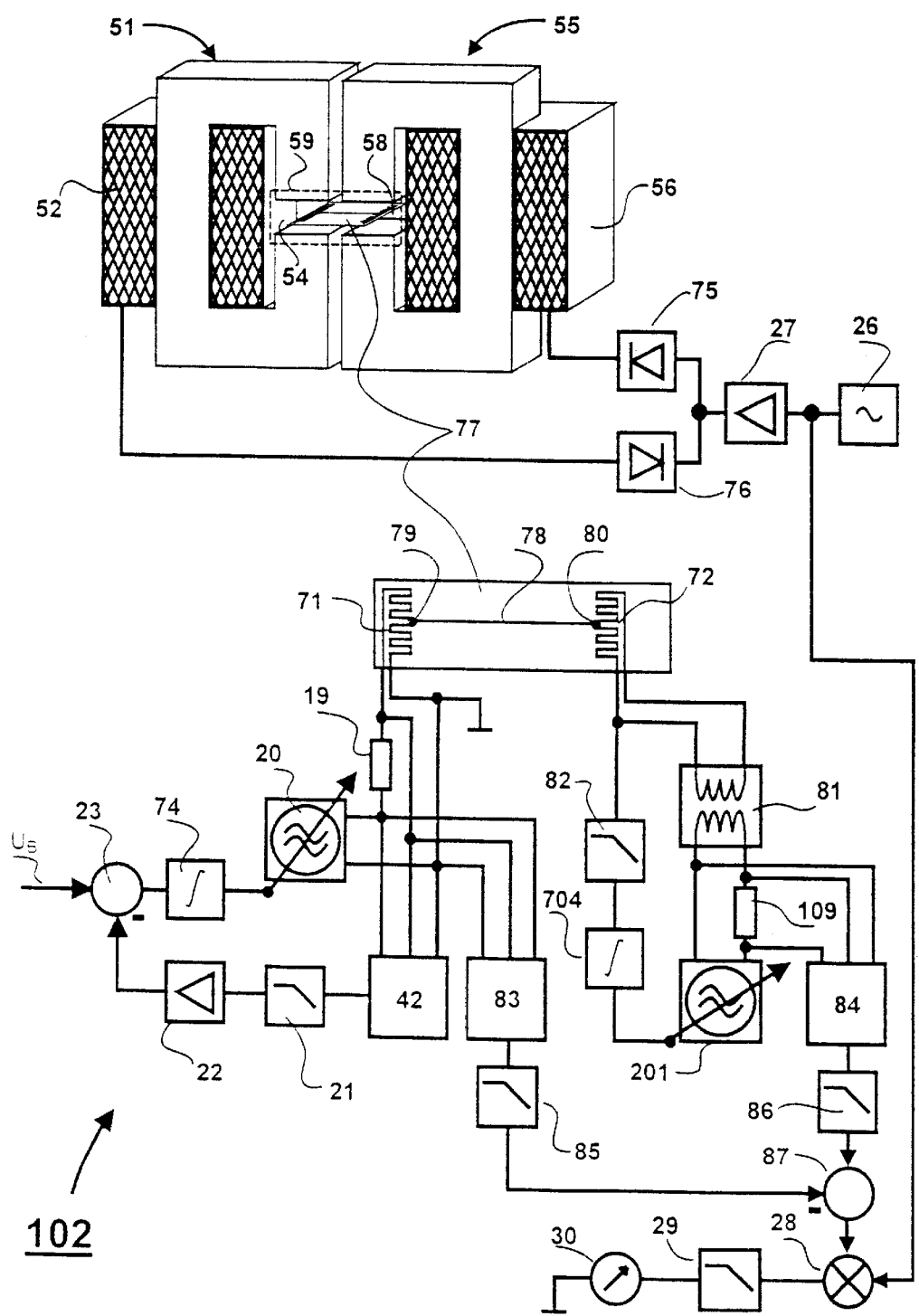
FIG. 11, an eleventh measuring apparatus as an alternative measuring apparatus to FIG. 10.

In the eleventh measuring apparatus 102. shown in FIG. 11, as compared to the tenth measuring apparatus 101 in FIG. 10, the first heating resistor 71 and the second heating resistor 72 are disposed on a measuring element carrier 77, and a thermocouple wire 78 is fastened between the heating resistors 71, 72; this wire is connected to the first heating resistor 71 by means of a first connection point 79 and to the second heating resistor 72 by means of a second connection point 80. The first heating resistor 71 and the first connection point 79 are both located in the first air gap 54, while the second heating resistor 72 and the second connection point 80 are disposed in the second air gap 58. For the sake of greater clarity, the measuring element carrier 77 is shown enlarged outside the measuring chamber 59 in FIG. 11. Identical components are provided with the same reference numerals as in FIGS. 9 and 10. With the closed control circuit formed by the components 19, 20, 21, 22, 23, 42, 71, 74, the first heating resistor 71 is regulated to a constant resistance, predetermined by the reference voltage $U_B$. To that end, the resistance is measured with the resistance measuring instrument 42 and compared with the set-point value of the reference voltage $U_B$. In the event of deviations, the alternating current source 20 is reregulated via the integrator 74.

The second heating resistor 72 is connected to an alternating current source 201 via a transformer 81 and a series resistor 109. A thermocouple arrangement, comprising the thermocouple wire 78 with the connection points 79, 80, measures the temperature difference between the heating resistors 71, 72. The thermocouple voltage, which is proportional to the temperature difference, is filtered by means of a low-pass filter 82 and is converted after signal processing in an integrator 704 into an adjusting variable for the alternating current source 201. If any temperature differences exist, the alternating source 201 is suitably readjusted, until the thermocouple voltage has become zero.

The electrical power converted in heating resistor 71 as well as the electrical power converted in heating resistor 72 reflect the thermal conduction conditions in the air gaps 54. 58. The electrical power respectively converted in the heating resistors 71, 72 is detected with the measuring instruments 83, 84. After signal filtration in the low-pass filters 85, 86 and finding of a difference at a comparison point 87, the differential signal is rectified phase-sensitively in the lock-in amplifier 28. Compared with the tenth measuring apparatus 101, the advantage is that temperature changes are compensated for, and the response time is shortened.

Figure 12:
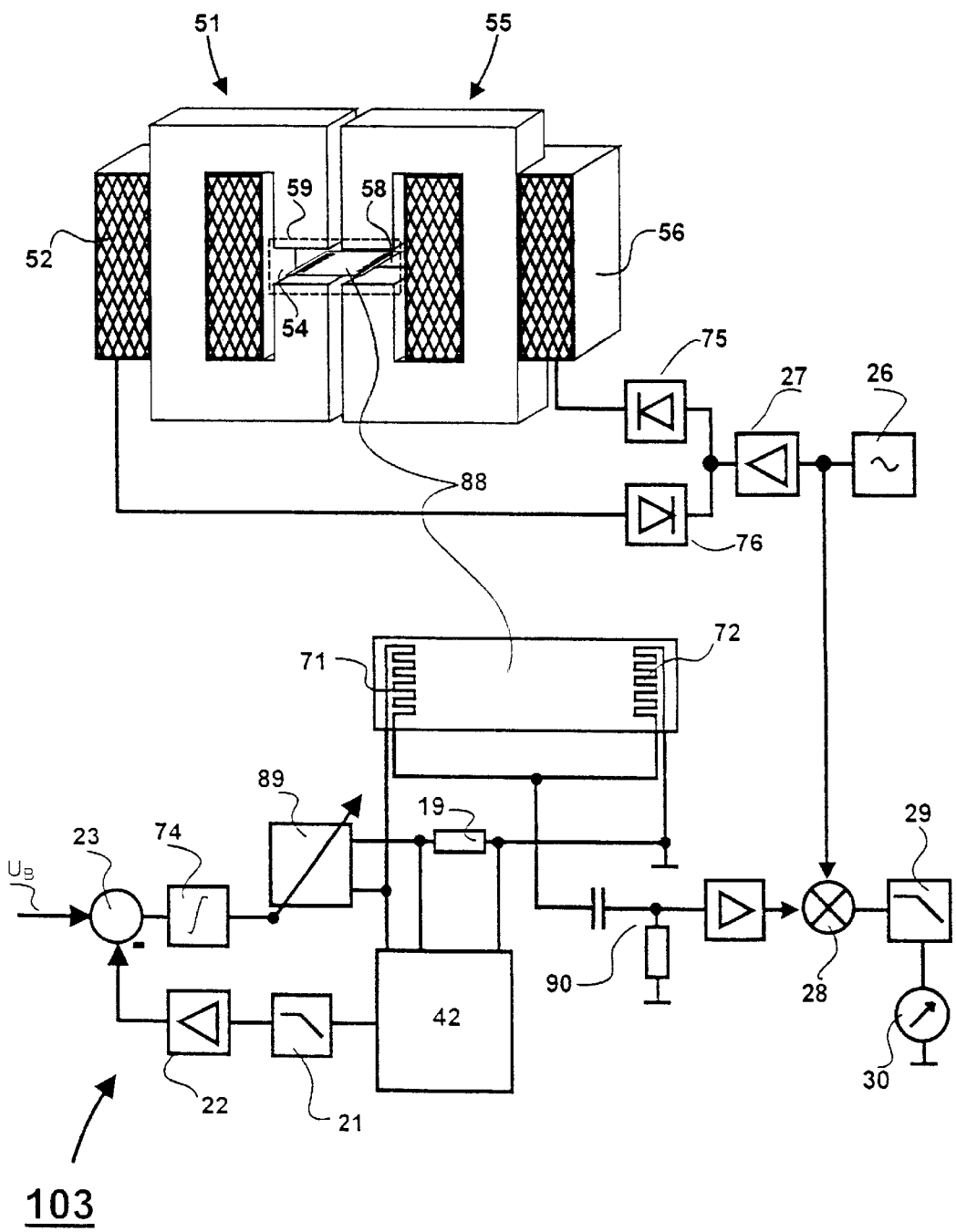
FIG. 12, a twelfth measuring apparatus with two heating elements as the measuring element.

FIG. 12 shows a twelfth measuring apparatus 103, in which only the heating resistors 71, 72 are disposed on a measuring element carrier 88; they are located respectively in the first air gap 54 and the second air gap 58. Via the series resistor 19, the heating resistors 71, 72 are connected to a direct current source 89, which receives an adjusting variable via the integrator 74. With the resistance measuring instrument 42, the total resistance of the heating resistors 71, 72 is measured and regulated to a constant value. The associated closed control circuit whose set-point value is the reference voltage $U_B$ is formed by the components 19, 21, 23, 42, 71, 72, 74, 88. The varying magnetic field in the air gaps 54, 58 changes the thermal conduction in the presence of a paramagnetic gas in the gas sample and causes a change of temperature and thus of resistance of the heating resistors 71, 72. A high-pass filter 90 filters out the direct voltage components, and after phase-sensitive rectification in the lock-in amplifier 28, a measurement variable proportional to the proportion of the paramagnetic gas can be read from the gauge or display unit 30.

What is claimed is:

1. An apparatus for measuring the proportion of a paramagnetic gas in a gas sample, comprising:
   a modulatable magnetic field source with an air gap;
   a modulation source for outputting a modulation signal to the magnetic field source;
   a measuring element, disposed at least partly inside the air gap and heated by a current source to an operating temperature, for outputting a heat flow measurement signal; and
   a filter device, connected to the measuring element, for filtering periodic fluctuations, caused by the modulation of the magnetic field source, out of the heat flow measurement signal, the amplitude of the periodic fluctuations being a measure for the proportion of the paramagnetic gas in the gas sample.

2. The apparatus of claim 1, wherein the measuring element is a thermocouple arrangement.

3. The apparatus of claim 1, wherein the measuring element comprises a succession of identical thermocouples, which together form a thermopile.

4. The apparatus of claim 2, wherein the current source is an alternating current source, and the thermocouple voltage, as the intrinsic EMF of the thermocouple arrangement, furnishes a measurement value proportional to the operating temperature.

5. The apparatus of claim 1, wherein the filter device is a phase-sensitive rectifier in the form of a lock-in amplifier.

6. The apparatus of claim 2, wherein a first closed control circuit for regulating the operating temperature of the thermocouple arrangement to a constant value, with the thermocouple voltage as a controlling variable, is present, and the heat flow measurement signal is the heating capacity delivered to the thermocouple arrangement.

7. The apparatus of claim 2, wherein a second closed control circuit for regulating the heating capacity delivered to the thermocouple arrangement to a constant value is provided, and the heat flow measurement signal is the thermocouple voltage.

8. The apparatus of claim 2, wherein a third closed control circuit for regulating the heating current, flowing through the thermocouple arrangement, to a constant value is provided, and the heat flow measurement signal is the thermocouple voltage.

9. The apparatus of claim 2, wherein a fourth closed control circuit for regulating the heating voltage applied to the thermocouple arrangement to a constant value is provided, and the heat flow measurement signal is the thermocouple voltage.

10. The apparatus of claim 2, wherein a fifth closed control circuit for regulating the operating temperature of the thermocouple arrangement to a constant value is provided, with the resistance of the thermocouple arrangement as a controlling variable, and the heat flow measurement signal is the thermocouple voltage.

11. The apparatus of claim 4, wherein for distinguishing the alternating heating voltage from the thermocouple voltage, a symmetrically wired measuring bridge is provided, in whose bridge branches Ohmic resistors and capacitors, each serial, are disposed, and one of the Ohmic resistors contains the thermocouple arrangement; and that the voltages dropping at the Ohmic resistors are delivered to a subtractor for subtraction.

12. The apparatus of claim 1, wherein the modulation source is an alternating current source with a sinusoidal voltage course.

13. The apparatus of claim 1, wherein the modulation source is a chopper disk rotating in the air gap.

14. A method for measuring the proportion of a paramagnetic gas in a gas sample, comprising the following steps:
    disposing a measuring element, heated to an operating temperature, in an air gap, receiving the gas sample, of a modulated magnetic field source;
    determining a heat flow measurement signal from the heat flow from the measuring element to the gas sample;
    with a filter device, filtering out periodic fluctuations from the heat flow measurement signal that are caused by the modulation of the magnetic field source; and from the periodic fluctuations, determining a concentration measurement value that indicates the proportion of the paramagnetic gas.

15. The method of claim 14, wherein a thermocouple arrangement is used as the measuring element.

16. An apparatus for measuring the proportion of a paramagnetic gas in a gas sample, comprising:
    a first modulatable magnetic field source with a first air gap;
    a second modulatable magnetic field source with a second air gap;
    a modulation source for outputting a modulation signal to the magnetic field sources;
    a reversing switch means, which connects the modulation source to the first magnetic field source and the second magnetic field source in alternation;
    a measuring element, located in the air gaps, for outputting a heat flow measurement signal, which measuring element comprises a thermocouple arrangement with at least one first connection point and one second connection point, the thermocouple arrangement being positioned such that the first connection point is located in the first air gap and the second connection point is located in the second air gap;
    an alternating current source, connected to the thermocouple arrangement, by which source the thermocouple arrangement is heated to an operating temperature that is elevated compared to the gas sample;
    a filter device, connected to the thermocouple arrangement, for filtering out periodic fluctuations from the heat flow measurement signal caused by the modulation of the magnetic field sources, the amplitude of the periodic fluctuations being a measure for the proportion of the paramagnetic gas in the gas sample.

17. The apparatus of claim 16, wherein a closed circuit is provided for regulating the operating temperature of the thermocouple arrangement to a constant value, using the resistance of the thermocouple arrangement as the controlling variable.

18. The apparatus of claim 16, wherein the thermocouple arrangement is embodied as a thermopile with opposed first connection points and second connection points.

19. An apparatus for measuring the proportion of a paramagnetic gas in a gas sample, comprising:

a first modulatable magnetic field source with a first air gap;

a second modulatable magnetic field source with a second air gap;

a modulation source for outputting a modulation signal to the magnetic field sources;

a reversing switch means, which connects the modulation source to the first magnetic field source and the second magnetic field source in alternation;

a measuring element, located in the air gaps, for outputting a heat flow measurement signal, which measuring element comprises a thermocouple arrangement with first connection points and second connection points, the thermocouple arrangement being positioned such that the first connection points are located in the first air gap and the second connection points are located in the second air gap;

a heat source, connected to the thermocouple arrangement, by which source the thermocouple arrangement is heated to an operating temperature that is elevated compared to the gas sample:

a filter device, connected to the thermocouple arrangement, for filtering out periodic fluctuations from the heat flow measurement signal caused by the modulation of the magnetic field sources, the amplitude of the periodic fluctuations being a measure for the proportion of the paramagnetic gas in the gas sample.

20. The apparatus of claim 19, wherein the heat source is embodied as a first heating resistor and a second heating resistor, the first heating resistor being disposed in the first air gap and the second heating resistor being disposed in the second air gap.

21. An apparatus for measuring the proportion of a paramagnetic gas in a gas sample, comprising:

a first modulatable magnetic field source with a first air gap;

a second modulatable magnetic field source with a second air gap;

a modulation source for outputting a modulation signal to the magnetic field sources;

a reversing switch means, which connects the modulation source to the first magnetic field source and the second magnetic field source in alternation;

a measuring element. located in the air gaps, for outputting a heat flow measurement signal, the measuring element comprising a first heat source, a second heat source. a thermocouple wire between the heat sources, with a first connection point between the thermocouple wire and the first heat source and with a second connection point between the thermocouple wire and the second heat source, the first heat source being located together with the first connection point in the first air gap and the second heat source and the second connection point being disposed in the second air gap, and the connection points are heated by the heat sources to an operating temperature that is elevated compared to the temperature of the gas sample;

means for detecting the difference in the heating power levels of the first heat source and the second heat source in the form of a heat flow measurement signal;

a filter device, connected to the thermocouple arrangement, for filtering out periodic fluctuations from the heat flow measurement signal caused by the modulation of the magnetic field sources, the amplitude of the periodic fluctuations being a measure for the proportion of the paramagnetic gas in the gas sample.

22. The apparatus of claim 21, wherein the first heat source is a first heating resistor, and the second heat source is a second heating resistor.

23. An apparatus for measuring the proportion of a paramagnetic gas in a gas sample, comprising:

a first modulatable magnetic field source with a first air gap;

a second modulatable magnetic field source with a second air gap;

a modulation source for outputting a modulation signal to the magnetic field sources;

a reversing switch means, which connects the modulation source to the first magnetic field source and the second magnetic field source in alternation;

a measuring element, located in the air gaps, for outputting a heat flow measurement signal, the measuring element comprising a first heat source and a second heat source, the measuring element being positioned such that the first heat source is located in the first air gap and the second heat source is located in the second air gap;

a direct current source, connected to the heat sources, by which direct current source the heat sources are heated to an operating temperature elevated compared to the temperature of the gas sample; and a filter device, connected to the heat sources, for filtering out periodic fluctuations from the heat flow measurement signal caused by the modulation of the magnetic field sources, the amplitude of the periodic fluctuations being a measure for the proportion of the paramagnetic gas in the gas sample.

24. The apparatus of claim 23, wherein the first heat source is a first heating resistor, and the second heat source is a second heating resistor.

25. Use of an apparatus as claimed in claim 1 for determining the oxygen concentration in a medical therapeutic appliance.

* * * * *